United States Patent

Daumy et al.

Patent Number: 5,622,830
Date of Patent: Apr. 22, 1997

[54] METHOD OF IDENTIFYING INTERLEUKIN 1β CONVERTING ENZYME INHIBITORS

[76] Inventors: Gaston O. Daumy; Laurence A. Reiter, both of 235 E. 42nd St., New York, N.Y. 10017-5755

[21] Appl. No.: 470,890

[22] Filed: Jun. 6, 1995

Related U.S. Application Data

[62] Division of Ser. No. 354,685, Dec. 12, 1994, Pat. No. 5,498,695.

[51] Int. Cl.$^6$ .......................... G01N 33/573; C12Q 1/37
[52] U.S. Cl. ................ 435/7.4; 435/18; 435/24; 530/330; 530/351; 514/18
[58] Field of Search .................. 435/24, 18; 530/330, 530/351; 514/18; 436/164, 7.4

[56] References Cited

U.S. PATENT DOCUMENTS 5,120,644  6/1992  Ikenaka et al. .......................... 435/24

OTHER PUBLICATIONS

Thornbery et al "A novel heterodimeric cysteine protease is required for interleukin 1β processing in Monocytes" Nature 356:768–774 1992.

*Primary Examiner*—James C. Housel
*Assistant Examiner*—Rodney P. Swartz
*Attorney, Agent, or Firm*—Peter C. Richardson; Gregg C. Benson; Robert F. Sheyka

[57] ABSTRACT

A compound of the formula $$R^1\text{—}A^2\text{—}A^1\text{—}\text{Asp-p-nitroanilide} \qquad \text{I}$$

wherein:
$A^1$ is a residue of any of the naturally occurring α-amino acids or a homolog, analog or derivative of a natural α-amino acid;
$A^2$ is a residue of a lipophilic α-amino acid;
$R^1$ is alkylcarbonyl, phenalkylcarbonyl, alkoxycarbonyl, phenalkoxycarbonyl, alkylaminocarbonyl, phenalkylaminocarbcnyl or $R^2$—$A^3$ wherein
$A^3$ is a residue of a lipophilic α-amino acid; and
$R^2$ is alkylcarbonyl, alkoxycarbonyl or phenylalkoxycarbonyl, and a method of detecting inhibitors of interleukin 1β converting enzyme (ICE) comprising evaluating a test compound's capacity to inhibit the ICE-induced hydrolysis of a compound of the formula I. The greater the ability of a test compound to inhibit such hydrolysis, the greater its expected activity in treating inflammation as well as diseases whose pathogenesis is induced or sustained by interleukin-1β. Also disclosed is the following intermediate, useful for synthesizing the compounds of formula I:

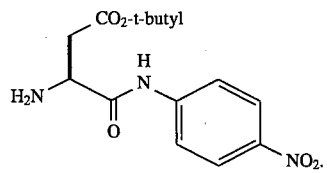

1 Claim, No Drawings

METHOD OF IDENTIFYING INTERLEUKIN 1β CONVERTING ENZYME INHIBITORS

This is a division of application Ser. No. 08/354,685, filed on Dec. 12, 1994, now U.S. Pat. No. 5,498,695.

BACKGROUND OF THE INVENTION

This invention is concerned with para-nitroanilide peptides and methods of using such peptides to detect inhibitors of interleukin 1β converting enzyme (ICE). Such inhibitors are useful in treating inflammatory conditions in mammals, especially man.

Current therapies for arthritis are severely limited by the side effects of available drugs and their ineffectiveness beyond treatment for disease symptoms. The most widely used drugs are agents (the non-steroidal antiinflammatory drugs, NSAIDS) which inhibit the cyclooxygenase pathway of arachidonic acid metabolism. While these compounds are effective in controlling the symptoms of arthritis, they are not disease remittive. Furthermore, cyclooxygenase inhibition is generally associated with the major side-effect of NSAID therapy, gastrointestinal irritation. Steroids are used in the more severe cases of arthritis and are very effective. However, long term therapy using steroids is seldom tolerable. Second line antiinflammatory agents such as gold, penicillamine, chloroquine and methotrexate are also beset with side effect issues which severely limit their general utility.

Interleukin-1 (IL-1) has been strongly implicated as a key mediator of tissue damage in osteo- and rheumatoid arthritis. Lowering levels of IL-1 in a diseased joint would be expected to halt continued degeneration and perhaps allow joint repair to take place. One approach to reducing levels of IL-1 is to block the generation of mature IL-1β from its biologically inactive precursor, pro-IL-1β, by inhibition of the interleukin-1β converting enzyme (ICE). This invention relates to a novel series of compounds which are substrates for ICE. The compounds may be used to detect ICE inhibitors which are useful for the treatment of diseases characterized by inflammation as well as diseases whose pathogenesis is induced or sustained by interleukin-1β. Such diseases include inflammatory bowel disease, psoriasis, allergic encephalitis, gingivitis, systemic lupus erythematosus, diabetes melitis, gout, septic shock and adult respiratory distress syndrome. It is expected that such inhibitors will not elicit the side effects associated with NSAID therapy (due to cyclooxygenase inhibition), steroids or other treatments currently in use.

SUMMARY OF THE INVENTION

The present invention relates to a compound of the formula

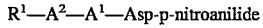

wherein:
$A^1$ is a residue of any of the naturally occurring α-amino acids (e.g., histidine, alanine, phenylalanine, glutamic acid, lysine, or aspartic acid) or a homologue, analog or derivative of a natural α-amino acid;

$A^2$ is a residue of a lipophilic α-amino acid (e.g. valine, alanine, leucine, isoleucine or phenylalanine);

$R^1$ is alkylcarbonyl, phenalkylcarbonyl, alkoxycarbonyl, phenalkoxycarbonyl, alkylaminocarbonyl, phenalkylaminocarbonyl or $R^2$—$A^3$ wherein $A^3$ is a residue of a lipophilic α-amino acid (e.g. tyrosine, phenylalanine, leucine, isoleucine or valine); and $R^2$ is alkylcarbonyl, alkoxycarbonyl or phenylalkoxycarbonyl.

The following are preferred compounds of the invention:

AcTyrValAlaAsp-p-nitroanilide;
PhCH$_2$CH$_2$COValAlaAsp-p-nitroanilide;
PhCH$_2$NHCOValAlaAsp-p-nitroanilide$_3$;
t-BOCValAlaAsp-p-nitroanilide;
AcValAlaAsp-p-nitroanilide; and
CBZValAlaAsp-p-nitroanilide.

The present invention also relates to a method of detecting inhibitors of interleukin 1β converting enzyme (ICE) comprising evaluating a compound's capacity to inhibit the ICE-induced hydrolysis of a compound of the formula I. The greater the ability of a compound to inhibit such hydrolysis, the greater its expected activity in treating inflammation as well as diseases whose pathogenesis is induced or sustained by interleukin-1β.

The abbreviations used herein to denote amino acids are well known and standard in the art and include the following: Ala, alanine; Pro, proline; His, histidine; Cys, cysteine; Cys(Me), methylcysteine; Phe, phenylalanine; Val, valine; Ile, isoleucine; Leu, leucine; Tyr, tyrosine; Glu, glutamic acid; Lys, lysine; Asp, aspartic acid; and Val, valine.

Other abbreviations used herein include the following: FMOC, fluorenylmethyloxycarbonyl; CBZ, benzyloxycarbonyl; Ac, acetyl; Ph, phenyl; t-BOC, t-butoxycarbonyl.

Many homologues, analogues and derivatives of natural α-amino acids are readily available, either from commercial sources or because they may be prepared by standard methods well-known to those of ordinary skill in the art. Examples of such compounds include phenylglycine, t-butylglycine, p-chlorophenylalanine, α-methylleucine, 1-aminocyclopentane-1-carboxylic acid.

The present invention also relates to the following intermediate, useful for synthesizing the compounds of formula I:

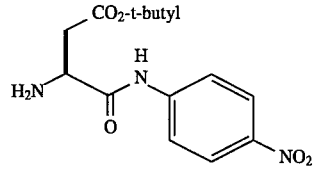

DETAILED DESCRIPTION OF THE INVENTION

The compounds of the present invention, having the formula I, as defined above, are readily and generally prepared by the general methods described below.

Scheme 1

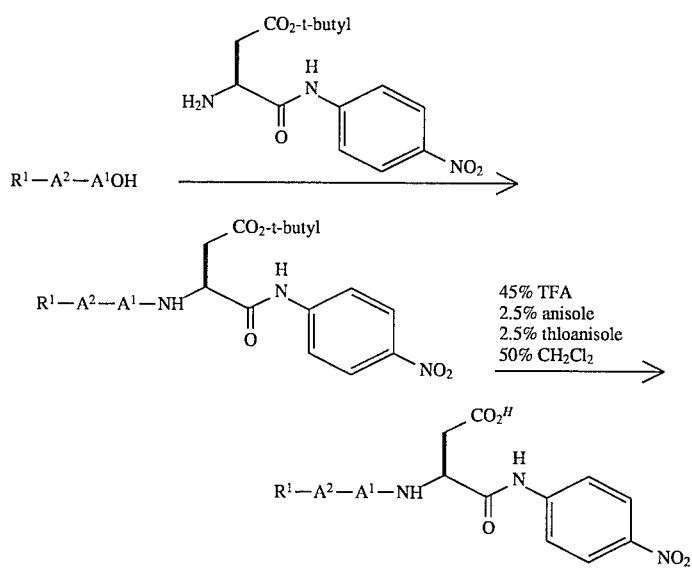

The most preferred procedure, shown in Scheme 1, is to first couple a di- or tripepride ($R^1$—$A^2$—$A^1OH$), which can be prepared by standard methods known in the art, with the β-t-butyl ester of aspartyl-p-nitroanilide (the product of Preparation 1). This coupling can be induced by any number of methods known in the art such as, but not limited to, those based on dicyclohexylcarbondiimide, 1-(dimethylaminopropyl)-3-ethylcarbodiimide hydrochloride (DEC.HCl) (the method used herein), isobutyl chloroformate, and N,N-bis [2-oxo-3-oxazolidinyl]phophorodiamidic chloride. Additives such as, but not limited to, N-hydroxysuccinimide or N-hydroxybenzotriazole, which are typically used in such couplings can be included. The solvent used for this coupling can be any reaction inert solvent such as, but not limited to, DMF (dimethylformanide), THF (tetrahydrofuran), dioxane, and methylene chloride. The coupling reaction can be performed at from about −20° to about 100° C., with temperatures about 15° to about 30° C. being preferred. The second step of the preferred procedure involves cleaving the β-t-butyl ester of the aspartyl residue which is carried out with strong acids such as, but not limited to, trifluoroacetic acid (TFA), hydrogen chloride, hydrogen bromide, p-toluenesulfonic acid, and methanesulfonic acid. Co-solvents such as, but not limited to, methylene chloride, dioxane and ethyl acetate can be used. TFA/methylene chloride mixtures are preferred. The reaction can be performed at from about −50° to about +50° C., with about 15° to about 30° C. being preferred. Additives such as, but not limited to, anisole and thioanisole can be included to prevent side reactions from occurring during the cleavage of the ester.

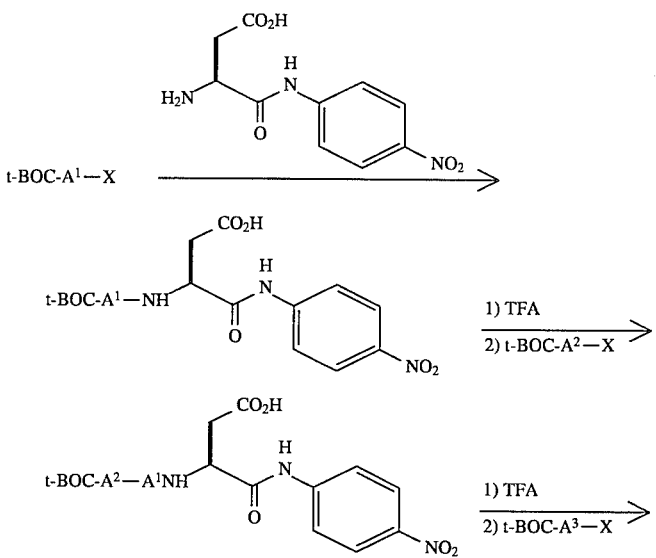

-continued

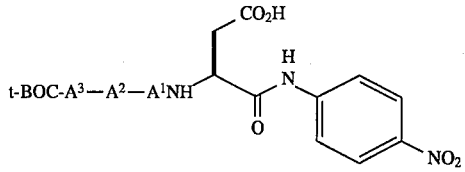

X = e.g. N-hydroxysuccinimide, pentaflurophenyl

In those cases where $R^1$ or $R^2$ is a t-butoxycarbonyl (t-BOC) group the preferred procedure is to first react aspartyl-p-nitroanilide hydrochloride (the product of Example 4, Step B) with a preactivated N-t-BOC-protected amino acid derivative in the presence of a base. This will give t-BOC-$A^1$-Asp-p-nitroanilide. Preactivation of the t-BOC-protected amino acid derivative may be as, but is not limited to, the N-hydroxysuccinimide or pentafluorophenyl esters. The base can be, but is not limited to, tertiary amine bases such as triethyl amine, diisopropyl ethyl amine, pyridine and N-methylmorpholine. The reaction is performed in a reaction inert solvent such as, but not limited to, DMF, THF, dioxane, and methylene chloride. The reaction can be performed at from about −20° to about 100° C. with temperatures about 15° to about 30° C. being preferred. In the second step the N-terminal t-BOC group is removed with strong acids such as, but not limited to, trifluoroacetic acid (TFA), hydrogen chloride, hydrogen bromide, p-toluenesulfonic acid, and methanesulfonic acid. Co-solvents such as, but not limited to, methylene chloride, dioxane and ethyl acetate can be used. TFA/methylene chloride mixtures are preferred. This reaction can be performed at from about −50° to about +50° C. with about 15° to about 30° C. being preferred. Co-solvents such as, but not limited to, anisole and thioanisole can be included to prevent side reactions from occurring during removal of the t-BOC group. In a third step, the product of this reaction is coupled as described above with a preactivated N-t-BOC-protected amino acid derivative in the presence of a base which will give t-BOC-$A^1$-Asp-p-nitroanilide. The two step sequence can be repeated again to give t-BOC-$A^3$-$A^2$-$A^1$-Asp-p-nitroanilide.

The compounds of formula 1 are substrates for ICE and, in conjunction with ICE that has been partially to totally purified or more preferably that has been immobilized in an active form by adsorption onto antibody coated protein A functionalized agarose beads, can be used for detecting inhibitors of ICE. Inhibitors of ICE may be used in treating inflammatory diseases in which interleukin-1β plays a role. Adsorption of ICE onto protein A functionalized agarose beads is achieved by coating the beads with a polyclonal antibody specific to the N-terminal region of ICE wherein the $F_c$ region of the antibody binds to the protein A. The $F_{ab}$ portion of the antibody remains free to bind to ICE which it does when the beads are then treated with a partially purified preparation of ICE derived from THP-1 cells. The ICE so bound retains its catalytic activity.

The following Preparations and Examples illustrate the preparation of the compounds of the present invention and their use in detecting ICE inhibitors. Abbreviations used below are defined either the first time they are used or on pages 2, 4 and 6 above.

PREPARATION 1

HAsp (β-t-butyl)-p-nitroanilide

A. FMOCAsp(β-t-butyl)-p-nitroanilide

Using the procedure of Rijkers et al. (*Recl. Trav. Chim Pays-Bas*, 110, 347 (1991)) FMOCAsp(β-t-butyl)OH (10.29 g, 25.0 mmole), p-nitroaniline (3.45 g, 25.0 mmole) and $POCl_3$ (4.22 g=2.56 mL, 27.5 mmole) in pyridine (75 mL) gave, after being passed through a pad of silica gel (40:60—ethyl acetate:hexane), 12.38 g (93%) of light yellow foam. Recrystallization of a portion from cyclohexene/ethyl acetate gave an analytical sample as a light yellow powder: mp 163°–164° C. (dec. with gas evol.); $^1$H NMR (CDCl$_3$) δ 1.47 (s, 9H), 2.68 (dd, J=7.4, 16.8 Hz, 1H), 2.97 (dd, J=3.8, 16.8 Hz, 1H), 4.24 (t, J=6.8 Hz, 1H), 4.51 (d, J=6.8 Hz, 2H), 4.6–4.7 (m, 1H), 6.0–6.15 (m, 1H), 7.25–7.35 (m, 2H), 7.35–7.45 (m, 2H), 7.58 (d, J=7.4 Hz, 2H), 7.67 (d, J=9.2 Hz, 2H), 7.77 (d, J=7.6 Hz, 2H, 8.21 (d, J=9.2 Hz, 2H), 9.0–9.1 (br s, 1H); MS (LSIMS) m/e 532 (11, M$^+$+1), 476 (29), 179 (100); $[α]_D^{20}$ +39.2° (c=1.0, DMF); Analysis calculated for $C_{29}H_{29}N_3O_7$: C, 65.52; H, 5.50; N, 7.91; found: C, 65.61; H, 5.58; N, 7.80.

B. HAsp(β-t-butyl)-p-nitroanilide

FMOCAsp(β-t-butyl)-p-nitroanilide (2.13 g, 4.0 mmole) and DBU (1,8-diazabicyclo[5.4.0]undecene-7) (609 g, 4.0 mmole) were stirred together in dry dimethylformanide (DMF)(40 mL) for 1 hour. The reaction mixture was then diluted with ether (200 mL) and extracted with 1N HCl (3×20 mL). The combined aqueous extracts were washed with ether and then basified with a calculated amount of $K_2CO_3$ (8.3 g, 60 mmole). This aqueous solution was extracted with ether (9×50 mL). The combined ether extracts were dried over $MgSO_4$. Filtration and concentration gave a yellow oil consisting of the desired product, some DBU and DMF. This was taken up in 1:1 ethyl acetate:hexane (50 mL) and poured onto a pad of silica gel. Elution with 1:1 ethyl acetate:hexane (7×50 mL) and ethyl acetate (3×200 mL) completely eluted the product. Concentration of the appropriate fractions gave 955 mg (77%) of light yellow solid. Recrystallization from cyclohexane/ethyl acetate gave an analytical sample as a pale yellow powder: mp 143°–144° C.; $^1$H NMR (CDCl$_3$) δ 1.44 (s, 9H), 2.1–2.3 (brs, 2H), 2.82 (dd, J=6.7, 16.9 Hz, 1H), 2.89 (dd, J=4.4, 16.9 Hz, 1H), 3.82 (dd, J=4.4, 6.7 Hz, 1H), 7.77 (d, J=9.2 Hz, 2H), 8.20 (d, J=92 Hz, 2H), 10.0–10.1 (br s, 1H); MS (LSIMS) m/e 310 (43, M$^+$+1), 254 (97), 154 (100); $[α]_D^{20}$ −4.9° (c=1.0, DMF); HPLC ret. time: 2.07 min (40%), 5.56 min (50%); Analysis calculated for $C_{14}H_{19}N_3O_5$: C,54.36; H, 6.19; N, 13.59; found C, 54.69; H, 6.22; N, 13.37.

PREPARATION 2

CBZValAlaOCH$_3$

CBZVal N-hydroxysuccinimide ester (8.71 g, 25.0 mmole), alanine methyl ester hydrochloride (3.49 g, 25.0 mmole), DIEA (diisopropylethylamine) (3.23 g. 25.0 mmole) were combined in $CH_2Cl_2$ (250 ml) and stirred at room temperature for 20 hours. The reaction mixture was washed twice, each time first with saturated $NaHCO_3$ and then with 1N HCl, and was then dried over $MgSO_4$, filtered, and concentrated giving a white solid. This was recrystallized from ethylacetate to give 5.49 g (65%) of fine white needles. A second crop of 1.56 g (18%) of fine white needles was obtained from the mother liquors: mp 163°–164° C.; $^1$H NMR ($CDCl_3$) δ 0.93 (d, J=6.8 Hz, 3H), 0.98 (d, J=6.8 Hz, 3H), 1.40 (d, J=7.2 Hz, 3H), 2.11 (hept, J=6.7 Hz, 1H), 3.74 (s, 3H), 4.01 (br t, 1H), 4.58 (pent, J=7.2 Hz, 1H), 5.11 (s, 2H), 5.38 (b d, 1H), 6.38 (br d, 1H), 7.3–7.4 (m, 5H); MS (LSIMS) m/e 337 (100, M$^+$+1), 255(66); $[\alpha]_D^{20}$ –46.0° (c=1.0, methanol); Analysis calculated for $C_{17}H_{24}N_2O_5$: C, 60.70; H, 7.19; N, 8.33; found: C, 60.70; H, 7.14; N, 8.33.

EXAMPLE 1

AcTyrValAlaAsp-p-nitroanilide

A. CBZTyr(O-t-butyl)ValAlaOCH$_3$

CBZValAlaOCH$_3$ (6.67 g, 19.8 mmole) was hydrogenated at 3 atm. over 10% Pd on carbon (700 mg) in $CH_3OH$ (100 mL) at room temperature. After 1 hour, the catalyst was removed by filtration through a nylon filter. The filtrate was evaporated in vacuo giving a white solid which was dissolved in a 1:1 mixture of $CH_2Cl_2$ and DMF (200 mL). To this solution was added CBZTyr(O-t-butyl) N-hydroxysuccinimide ester (9.28 g, 19.8 mmole). After being stirred at room temperature for 18 hours, the mixture was concentrated in vacuo to remove the $CH_2Cl_2$ and then water (300 mL) was added to precipitate the product. The solid was collected, washed with water and dissolved in ethyl acetate (500 mL). This solution was washed twice with saturated $NaHCO_3$ and twice with 1N HCl and dried over $MgSO_4$. Filtration and evaporation in vacuo gave a white solid which was recrystallized from cyclohexene (100 mL) ethyl acetate (70 mL) yielding 7.10 g (65%) of white fluffy solid. A second crop of 1.25 g (11%) was obtained from the mother liquors: mp 189°–190° C.; $^1$H NMR (DMSO-d$_6$) δ 0.85 (d, J=6.8 Hz, 3H), 0.88 (d, J=7.0 Hz, 3H), 1.2–1.35 (m, 12H), 1,85–2.05 (m, 1H), 2.83 (dd, J=10.9, 13.8 Hz), 1H), 2.92 (dd, J=3.7, 13.8 Hz, 1H), 3.3–3–4 (m, 2 (partially obscured by $H_2O$ absorption)), 3.60 (s, 3H), 4.2–4.4 (m, 3H), 4.94 (s, 2H), 6.85 (d, J=8.4 Hz, 2H), 7.17 (d, J=8.4 Hz, 2h), 7.2–7,35 (m, 5H), 7.52 (d, J=8.7 Hz, 1H), 7.83 (d, J=9.2 Hz, 1H), 8.45 (d, J=6.5 Hz, 1H); MS (LSIMS) m/e 556 (100, M$^+$+1), 453 (31); $[\alpha]_D^{20}$ –35.1° (c=1.0 methanol); Analysis calculated for $C_{30}H_{41}N_3O_7$: C, 64.84; H, 7.44; N, 7.56; found C, 64.96; H, 7.35; N, 7.52.

B. AcTyr(O-t-butyl)ValAlaOCH$_3$

CBZTyr(O-t-butyl)ValAlaOCH$_3$ (5.55 g, 10.0 mmole) was hydrogenated at 3 atm. over 10% Pd on carbon (500 mg) in $CH_3OH$ (100 mL) at room temperature. After 1 hour, the catalyst was removed by filtration through a nylon filter. The filtrate was evaporated in vacuo giving an oil which was dissolved in THF (100 mL). To this solution was added DIEA (1.55 g, 12 mmole) and acetyl chloride (942 mg, 12 mmole). After being stirred at room temperature overnight, the reaction mixture was concentrated in vacuo and the residue dissolved in $CHCl_3$. This solution was washed with 1N HCl, and then with saturated $NaHCO_3$ and then dried over $MgSO_4$. Filtration and evaporation in vacuo gave a gel-like solid which was recrystallized from ethyl acetate/$CH_3OH$ to give 2.86 g (62%) of a gel-like solid which was dried under high vacuum. A second crop of 1.42 g (31%) was obtained from the mother liquors: mp 209°–211° C.; $^1$H NMR (DMSO-d$_6$) δ 0.82 (d, J=6.8 Hz, 3H), 0.86 (d, J=6.8 Hz, 3H) 1.24 (s, 9H), 1.27 (d, J=7.3 Hz, 3H), 1.73 (s, 3H), 1.94 (hept, J=6.8 Hz, 1H), 2.66 (dd, J=10.0, 14.0Hz, 1H), 2.90 (dd, J=4.3, 14.0 Hz, 1H), 3.59 (s, 3H), 4.15–4.3 (m, 2H), 4.5–4.6 (m, 1H), 6.82 (d, J=8.4 Hz, 2H), 7.12 (d, J=8.4 Hz, 2H), 7.79 (d, J=9.0 Hz, 1H), 8.06 (d, J=8.4 Hz, 1H) 8.39 (d, J=6.6 Hz, 1H); MS (LSIMS) m/e 464 (100, M$^+$+1); $[\alpha]_D$ –17.0° (c=1.0, DMF); Analysis calculated for $C_{24}H_{37}N_3O_6$: C, 62.18; H, 8.05; N, 9.06; found: C, 62.27; H, 8.18; N, 9.00.

C. AcTyr(O-t-butyl)ValAlaOH

AcTyr(O-t-butyl)ValAlaOCH$_3$ (2.32 g, 5.0 mmole) was slurried in 10% aqueous $CH_3OH$ (50 mL) and treated with LiOH.H$_2$O (1.05 g, 25.0 mmole) in one portion. The reaction mixture was stirred at room temperature for 2 hours and the reaction was then quenched by the addition of an excess of sulfonic acid ion exchange resin (56 g, 125 meq of H+). After being stirred for 15 minutes, the mixture was filtered and the resin washed thoroughly with $CH_3OH$. The filtrate was concentrated in vacuo to give a white solid which was recrystallized from ethyl acetate/$CH_3OH$ yielding, after drying under high vacuum, 1.96 g (87%) of a white powder: mp 191°–192° C. (dec. with gas evolution); $^1$H NMR (DMSO-d$_6$) δ 0.82 (d, J=6.8 Hz, 3H), 0.86 (d, J=6.8 Hz, 3H), 1.25 (s, 9H), 1.27 (d, J=7.3 Hz, 3H, partially obscured), 1.74 (s, 3H), 1.95 (hept, J=6.8 HZ, 1H), 2.66 (dd, J=10.1, 13.9 Hz, 1H), 2.92 (dd, J=4.2, 13.9 Hz, 1H), 4.1–4.25 (m, 2H), 4.5–4.6 (m, 1H), 6.82 (d, J=8.4 Hz, 2H), 7.12 (d, J=8.4 Hz, 2H), 7.79 (d, J=9.0 Hz, 1H), 8.07 (d, J=8.4 Hz, 1H), 8.23 (d, J=6.9 Hz, 1H); MS (LSIMS) m/e 450 (53, M$^+$+1), 189(100); $[\alpha]_D^{20}$ –8.7° (c=1, DMF); Analysis calculated for calculated for $C_{23}H_{35}N_3O_6$: C, 61.45; H, 7.85; N, 9.35; found C, 61.18; H, 8.05; N, 9.26.

D. AcTyr(O-t-butyl)ValAlaAsp(β-t-butyl)-p-nitroanilide

AcTyr(O-t-butyl)ValAlaOH (687 mg, 1.53 mmole), HAsp(β-t-butyl)-p-nitroanilide (473 mg, 1.53 mmole), N-hydroxysuccinimide (264 mg, 2.29 mmole) and DEC.HCl (352 mg, 1.84 mmole) were combined in dry DMF (15 mL) and the resulting pale yellow solution stirred at room temperature for 44 hours. The reaction mixture was diluted with 1N HCl and the resulting precipitated solid triturated to break all chunks of solid into a finely dispersed solid. This was then collected and washed with 1N HCl. The solid was resuspended in aqueous $NaHCO_3$, triturated for 15 minutes and collected. After washing with water and drying under high vacuum 875 mg (77%) of a white powder was obtained. A portion of this was recrystallized from ethyl acetate/$CH_3OH$ to give an analytical sample: mp 234°–235° C. (dec. with gas evolution); $^1$H NMR (DMSO-d$_6$) δ 0.82 (t,J=7.1 Hz, 3H), 1.21 (d, J=7.1 Hz, 3H), 1.24 (s, 9H), 1.34 (s, 9H), 1.74 (s, 3H), 2.57 (dd, J=7.6, 15.9 Hz, 1H), 2.63–2.72 (m, 1H), 2.76 (dd, J=6.8, 15.9 Hz, 1H), 2.92 (dd, J=0.6, 10.1 Hz, 1H), 4.1–4.2 (m, 1H), 4.2–4.3 (m, 1H), 4.5–4.6 (m, 1H), 4.6–4.7 (m, 1H), 6.82 (d, J=8.4 Hz, 2H), 7.13 (d, J=8.4 Hz, 2H), 7.88 (d, J=9.3 Hz, 2H), 8.08 (d, J=8.4 Hz, 1H), 8.14 (d, J=6.7 Hz, 1H), 8.22 (d, J=9.3 Hz, 1H), 8.38 (d, J=7.5 Hz, 1H), 10.52 (s, 1H); MS(LSIMS) m/e 741 (32, M$^+$+1), 710 (34), 432 (53), 361 (75), 305 (100); $[\alpha]_D^{20}$ –16.4° (c=1, DMF); Analysis calculated for $C_{37}H_{52}N_6O_{10}$: C, 59.98; H, 7.08; N, 11.35; found: C, 59.78; H, 6.90; N, 11.20.

E. AcTyrValAlaAsp-p-nitroanilide

A slurry of AcTyr(O-t-butyl)ValAlaAsp(β-t-butyl)-p-nitroanilide (148 mg, 0.20 mmole) in $CH_2Cl_2$ (10 mL) at 0° C. was treated with 10 mL of a prechilled mixture of TFA:anisole:thioanisole (90:5.5). The resulting solution was stirred at 0° C. for 30 minutes and at room temperature for 4 hours. The mixture was concentrated in vacuo. $CH_2Cl_2$ was added to the concentrate and the solvent evaporated in vacuo. The residue was then triturated with ether for a few hours. The solid was collected, washed thoroughly with ether and dried under vacuum to give 109 mg (87%) of a white powder; mp 205°–206° C. (dec.); $^1$H NMR (DMSO(dimethylsulfoxide)-d$_6$) δ 0.82 (t, J=7.3 Hz, 6H), 1.22 (d, J=7.2 Hz, 3H), 1.74 (s, 3H), 1.9–2.0 (m, 1H), 2.5–2.7 (m, 3H), 2.86 (dd, J=0.6, 10.2 Hz, 1H), 4.1–4.2 (m, 1H), 4.2–4.3 (m, 1H), 4.45–4.55 (m, 1H), 4.6–4.7 (m, 1H), 6.61 (d, J=8.4 Hz, 2H), 7.01 (d, J=8.4 Hz, 2H), 7.84 (d, J=9.2 Hz, 2H), 7.88 (d, 1H, partially obscured by adjacent peak), 8.06 (d, J=8.3 Hz, 1H), 8.12 (d, J=7.0 Hz, 1H), 8.20 (d, J=9.2 Hz, 2H) 8.31 (d, J=7.5 Hz, 1H), 11.2–11.4 (br s, 1H); MS (LSIMS) m/e 651 (5, M$^+$+Na), 629 (3, M$^+$+1), 491 (7), 424, (3), 376 (18), 305 (47), 178 (136), 136 (100); [α]$_D^{20}$ –18.8° (c=1.0, DMF); Analysis calculated for C$_{29}$H$_{36}$N$_6$O$_{10}$: C, 55.40; H, 5.77; N, 13.37: found C, 55:60; H, 6.24; N, 13.49.

EXAMPLE 2

PhCH$_2$CH$_2$COValAlaAsp-p-nitroanilide

A. PhCH$_2$CH$_2$COValAlaOCH$_3$

CBZValAlaOCH$_3$ (1.35 g, 4.00 mmole) was hydrogenated at 3 atm. over 10% Pd on carbon (150 mg) in CH$_3$OH (40mL) at room temperature. After 1 hour, the catalyst was removed by filtration through a nylon filter. The filtrate was evaporated in vacuo giving a white solid which was slurried in CHCl$_3$(40 mL) and treated with DIEA (620 mg, 4.8 mmole) and hydrocinnamoyl chloride (741 mg, 4.4 mmole). After 1 hour at room temperature, the reaction mixture was washed with 1N HCl, dried with MgSO$_4$ filtered and concentrated in vacuo to a white solid. This was recrystallized from ethylacetate to give 617 mg (48%) of white powder: mp 207°–208° C.; $^1$H NMR (DMSO-d$_6$) δ 0.79 (d, J=6.8 Hz, 3H), 0.84 (d, J=6.7 Hz, 3H), 1.28(d, J=7.3 Hz, 3H), 1.85–2.0 (m, 1H), 2.35–2.5 (m, 2H, partially obscured by the DMSO-d$_5$ peak), 2.75–2.85 (m, 2H), 3.61 (s, 3H), 4.15–4.3 (m, 2H), 7.1–7.3 (m, 5H), 7.90 (d, J=9.1 Hz, 1H), 8.43 (d, J=6.7 Hz, 1H); MS (FAB) m/e 335 (88, M$^+$+1), 232 (100), 204 (53); [α]$_D^{°}$–71.7° (c=1.0, methanol); Analysis calculated for C$_{18}$H$_{26}$N$_2$O$_4$: C, 64.65; H, 7.84; N, 8.38; found: C, 64.85; H, 7.62; N, 8.05.

B. PhCH$_2$CH$_2$COValAlaOH

By the same procedure used to prepare AcTyr(O-t-butyl)ValAlaOH, PhCH$_2$CH$_2$COValAlaOCH$_3$ (508 mg, 1.52 mmole) and LiOH.OH (319 mg, 7.6 mmole) in 10% aqueous CH$_3$OH (15 mL) gave, after quenching with sulfonic acid ion exchange resin (17.0 g, 38 meq), 511 mg (100%) of pure product as a white powder. Recyrstallization of a portion from ethylacetate gave an analytical sample: mp 205°–206° C.; $^1$H NMR (DMSO-d$_6$) δ 0.76 (d, J=6.7 Hz, 3H), 0.81 (d, J=6.8 Hz, 3H), 1.24 (d, J=7.3 Hz, 3H), 1.8–1.95 (m, 1H), 2.35–2.55 (m, 2H, partially obscured by the DMSO-d$_5$ peak), 2.75–2.85 (m, 2H), 4.1–4.25 (m, 2H), 7.1–7.3 (m, 5H), 7.84 (d, J=9.1 Hz, 1H), 8.23 (d, J=6.9Hz, 1H); MS (LSIMS) m/e 321 (45, M$^+$–1), 232 (29),204(11), 157(100); [α]$_D^{20}$ –2.0° (c=1.0, DMF); Analysis calculated for C$_{17}$H$_{24}$N$_2$O$_4$: C, 63.73; H, 7.55; N, 8.75; found: C, 63.78; H, 7.30; N, 8.60.

C. PhCH$_2$CH$_2$COValAlaAsp(β-t-butyl)-p-nitroanilide

By the same procedure used to prepare the title compound of Example 1D, PhCH$_2$CH$_2$COValAlaOH (401 mg, 1.20 mmole), HAsp(β-t-butyl)-p-nitroanilide (387 mg, 1.20 mmole), N-hydroxysuccinimide (216 mg, 1.5 mmole) and DEC.HCl (288 mg, 1.88 mmole) in DMF (12 mL) gave 661 mg (90%) of a tan powder. This was recrystallized from ethyl acetate to give 459 mg (62%) of a white powder; mp 222°–224° C. (dec. with gas evolution); $^1$H NMR (DMSO-d$_6$) δ 0.77 (t, J=6.9 Hz, 6H), 1.20 (d, J=7.1 Hz, 3H), 1.34 (s, 9H), 1.85–1.95 (m, 1H), 2.35–2.65 (m, 3, partially obscured by the DMSO-d$_5$ peak), 2.7–2.85 (m, 3H), 4.1–4.15 (m, 1H), 4.2–4.3 (m, 1H), 4.6–4.7 (m, 1H), 7.1–7.3 (m, 5H), 7.85–7.95 (m, 3H), 8.13 (d, J=6.8 Hz, 1H), 8.21 (d, J=9.3 Hz, 2H), 8.31 (d, J=7.6 Hz, 1H), 10.56 (s, 1H); MS (LSIMS) m/e 612 (4, M$^+$+1), 556 (16), 418 (15), 325(7), 303(26), 232(100), 204(62); [α]$_D^{20}$ –17.6° (c=1.0, DMF); Analysis calculated for C$_{31}$H$_{41}$N$_5$O$_8$: C, 60.87; H, 6.76; N, 11.45; found: C, 61.04; H, 6.59; N, 11.23.

D. PhCH$_2$CH$_2$COValAlaAsp-p-nitroanilide

By the same procedure used to prepare the compound of Example 1E, PhCH$_2$CH$_2$COValAlaAsp(β-t-butyl)-p-nitroanilide (122 mg, 0.2 mmole) gave 104 mg (94%) of a light tan powder: mp 206°–208° C. (dec.); $^1$H NMR (DMSO-d$_6$) δ 0.77 (t, J=7.0 Hz, 6H), 1.21 (d, J=7.1 Hz, 3H), 1.85–2.0 (m, 1H), 2.35–2.7 (m, 3, partially obscured by the DMSO-d$_5$ peak), 2.7–2.85 (m, 3H), 4.1–4.18 (m, 1H), 4.18–4.3 (m, 1H), 4.6–4.7 (m, 1H), 7.1–7.3 (m, 5H), 7.85–7.95 (m, 3H), 8.12 (d, J=6.7 Hz, 1H), 8.21 (d, J=9.3 Hz, 2H), 8.29 (d, J=7.6 Hz, 1H), 10.55 (s, 1H); MS (LSIMS) m/e 578 (10, M$^+$+Na), 418 (4), 303 (26), 232 (100), 204 (89); [α]$_D^{20}$ –21.6° (c=1.0, DMF); Analysis calculated for C$_{27}$H$_{33}$N$_5$O$_8$: C, 58.37; H, 5.99; N, 12.61; found: C, 58.29; H, 5.84; N, 12.43.

EXAMPLE 3

PhCH$_2$NHCOValAlaAsp-p-nitroanilide

A. PhCH$_2$NHCOValAlaOCH$_3$

CBZValAlaOCH$_3$ (1.35 g, 4.00 mmole) was hydrogenated at 3 atm. over 10% Pd on carbon (150 mg) in CH$_3$OH (40 mL) at room temperature. After 1 hour, the catalyst was removed by filtration through a nylon filter. The filtrate was evaporated in vacuo giving a white solid which was slurried in CHCl$_3$ (40 mL) and treated with benzyl isocyanate (586 mg, 4.4 mmole). After 1 hour at room temperature, the reaction mixture was washed three times with 1N HCl, dried over MgSO$_4$, filtered and concentrated in vacuo giving 791 mg (61%) of the desired product as a white powder. Recrystallization of a portion from ethyl acetate/CH$_3$OH gave an analytical sample: mp 227°–228° C.; $^1$H NMR (DMSO-d$_6$) δ 0.80 (d, J=6.8 Hz, 3H), 0.86 (d, J=6.7 Hz, 3H), 1.26(d, J=7.3 Hz, 3H), 1.85–1.95 (m, 1H), 3.59 (s, 3H), 4.10 (dd, J=5.9, 9.2 Hz, 1H), 4.15–4.3 (m, 3H), 6.08 (d, J=9.3 Hz, 1H), 6.53 (t, J=6.0 Hz, 1H), 7.15–7.35 (m, 5H), 8.39 (d, J=6.7 Hz, 1H); MS (LSIMS) m/e 336 (100, M$^+$+1), 233 (62), 203 (76); [α]$_D^{20}$ +6.1° (c=1.0, DMF); Analysis calculated for C$_{17}$H$_{25}$N$_3$O$_4$; C, 60.88; H, 7.51; N, 12.53; found: C, 60.98; H, 7.30; N, 12.34.

B. PhCH$_2$NHCOValAlaOH

By the same procedure used to prepare the title compound of Example 1C, PhCH$_2$NHCOValAlaOCH$_3$ (671 mg, 2.00 mmole) and LiOH.OH (168 mg, 4.00 mmole) in 10% aqueous CH$_3$OH (20 mL) gave after quenching with sulfonic acid ion exchange resin (18.0 g, 40 meq) 658 mg (100%) of pure product as an off-white flaky solid. Recrystallization of a portion from ethyl acetate/CH$_3$OH gave an analytical sample as very fine white crystals: mp 205°–206° C.; $^1$H NMR (DMSO-d$_6$) δ 0.79 (d, J=6.8 Hz, 3H), 0.86 (d, J=6.7 Hz, 3H), 1.25 (d, J=7.3 Hz, 3H), 1.85–2.0 (m, 1H), 4.05–4.3 (m, 4H), 6.09 (d, J=9.3 Hz, 1H), 6.54 (t, J=6.0 Hz, 1H), 7.15–7.35 (m, 5H), 824 (d, J=7.0 Hz, 1H);

MS (LSIMS) m/e 344 (22, M$^+$+Na), 322 (83, M$^+$+1), 233 (70), 205(18), 189 (100); [α]$_D^{20}$ +15.3° (c=1.0, DMF); Analysis calculated for C$_{16}$H$_{23}$N$_3$O$_4$: C, 59.79; H, 7.21; N, 13.08; found: C, 59.87; H, 7.30; N, 12.80.

C. PhCH$_2$NHCOValAlaAsp(β-t-butyl)-p-nitroanilide

By the same procedure used to prepare the title compound of Example ID, PhCH$_2$NHCOValAlaOH (553 mg, 1.72 mmole), HAsp(β-t-butyl)-p-nitroanilide (532 mg, 1.72 mmole), N-hydroxysuccinimide (247 mg, 2.15 mmole) and DEC.HCl (515 mg, 2.69 mmole) in DMF (17 mL) gave 1.04 g (99%) of a light yellow powder. This was recrystallized from ethyl acetate/CH$_3$OH to give 667 mg (63%) of a white powder: mp 209°–210° C. (dec. with gas evolution); $^1$H NMR (DMSO-d$_6$) δ 0.79 (d, J=6.8 Hz, 3H), 0.84 (d, J=6.7 Hz, 3H), 1.21 (d, J=7.1 Hz, 3H), 1.34 (s, 9H), 1.85–2.0 (m, 1H), 2.55 (dd, J=7.7, 16.0 Hz, 1H), 2.74 (dd, J=6.7, 16.0 Hz, 1H), 4.02 (dd, J=5.8, 8.3 Hz, 1H), 4.15–4.3 (m, 3H), 4.6–4.7 (m, 1H), 6.13 (d, J=8.4 Hz, 1H), 6.56 (t, J=6.0 Hz, 1H), 7.15–7.35 (m, 5H), 7.88 (d, J=9.3 Hz, 2H), 8.15–8.25 (m, 3H), 8.33 (d, J=7.6 Hz, 1H), 10.50 (s, 1H); MS (LSIMS) m/e 635 (1, M$^+$+Na), 613 (3, M$^+$+1), 557 (13), 424(12), 304 (13), 286 (19), 233 (100), 205 (29), 171 (27); [α]$_D^{20}$ –2.8° (c=1.0, DMF); Analysis calculated for C$_{30}$H$_{40}$N$_6$O$_8$: C, 58.81; H, 6.58; N,13.72; found: C, 58.92; H, 6.56; N, 13.64.

D. PhCh$_2$NHCOValAlaAsp-p-nitroanilide

By the same procedure used to prepare the title compound of Example IE, PhCH$_2$NHCOValAlaAsp(β-t-butyl)-p-nitroanilide (123 mg, 0.2 mmole) gave 102 mg (92%) of an off-white powder: mp 207°–209° C.; $^1$H NMR (DMSO-d$_6$) δ 0.78 (d, J=6.8 Hz, 3H), 0.84 (d, J=6.7 Hz, 3H), 1.22 (d, J=7.1 Hz, 3H), 1.85–2.0 (m, 1H), 2.60 (dd, J=7.7, 16.0 Hz, 1H), 2.78 (dd, J=6.7, 16.0 Hz, 1H), 4.02 (dd, J=5.8, 8.3 Hz, 1H), 4.15–4.3 (m, 3H), 4.6–4.7 (m, 1H), 6.12 (d, J=8.5 Hz, 1H), 6.56 (t, J=6.0 Hz, 1H), 7.15–7.35 (m, 5H), 7.88 (d, J=9.3 Hz, 2H), 8.15–8.25 (m, 3H), 8.33 (d, J=7.6 Hz, 1H), 10.47 (s, 1H), 12.45 (br s, 1H); MS (LSIMS) m/e 579 (4, M$^+$+Na), 557(15, M$^+$+1), 304 (14), 286 (20), 233 (100); [α]$_D^{20}$ –3.5° (c=1.0, DMF); Analysis calculated for C$_{26}$H$_{32}$N$_{60}$O$_8$.0.5H$_2$O; C, 55.01; H, 6.22; N, 14.81; found: C, 55.15, H, 6.06; N, 14.54.

EXAMPLE 4 t-BOCValAlaAsp-p-nitroanilide

A. t-BOCAsp(β-t-butyl)-p-nitroanilide

Using the procedure of Rijkers et al. (*Recl. Trav. Chim Pays-Bas*, 110, 347 (1991)) t-BOCAsp(β-t-butyl)OH (7.65 g, 25.0 mmole), p-nitroaniline (3.45 g, 25.0 mmole) and POCl$_3$ (4.22 g=2.56 mL, 27.5 mmole) in pyridine (75 mL) gave, after being passed through a pad of silica gel (25:75 ethyl acetate:hexane), 8.93 g (87%) of light yellow foam: $^1$H NMR (CDCl$_3$) δ 1.47 (s, 9H), 1.49 (s, 9H), 2.69 (dd, J=6.7, 17.0 Hz, 1H), 2.91 (dd, J=4.3, 17.0 Hz, 1H), 4.59 (m, 1H), 5.90 (br d, 1H), 7.69 (d, J=9.2 Hz, 2H), 8.20 (d, J=9.2 Hz, 2H), 9.20 (br s, 1H); MS (LSIMS) m/e 410 (22), 394 (9), 354 (18), 298 (100), 282 (17), 254 (26); [α]$_D^{20}$ –30.0° (c=1.0, methanol); Analysis calculated for C$_{19}$H$_{27}$N$_3$O$_7$: C, 55.73; H,6.65; N, 10.26; found: C, 55.50; H, 6.41; N, 10.22.

B. HAsp-p-nitroanilide Hydrochloride t-BOC-Asp(β-t-butyl)-p-nitroanilide (8.68 g, 21.2 mmole) was dissolved in a mixture of dioxane (200 mL) and ethyl acetate (50 mL) and cooled to 0° C. The solution was then saturated with HCl gas and stirred for one hour at 0° C. The HCl was then purged from the reaction with a stream of N$_2$ and the reaction mixture concentrated to a yellow glass. This was triturated with ether, collected and dried under high vacuum to give 6.79 g (yield greater than 100%; NMR indicated some ether still present) of a light yellow powder: $^1$H NMR (DMSO-d$_6$) δ 2.93 (dd, J=7.3, 17.5 Hz, 1H), 3.01 (dd, J=5.2, 17.5 Hz, 1H), 4.32 (m, 1H), 7.18 (d, J=9.1 Hz, 2H), 8.26 (d, J=9.1 Hz, 2H); MS (LSIMS) m/e 254 (54, M$^+$+1), 239 (92), 221 (100), 197 (94), 195 (76).

C. t-BOCAlaAsp-p-nitroanilide

HAsp-p-nitroanilide hydrochloride (2.90 g, 10.0 mmole), t-BOCAla N-hydroxysuccinimide ester (2.86 g, 10.0 mmole) and DIEA (1.29 g, 10.0 mmole) were combined in CH$_2$Cl$_2$ (100 mL) and stirred for 24 hours at room temperature. The resulting turbid solution was washed twice with 0.1N HCl and then dried over MgSO$_4$. Filtration and concentration in vacuo gave a yellow foam that was chromatographed (5:30:65—acetic acid:ethyl acetate:hexane to 5:35:60—acetic acid:ethylacetate:hexane) to give 3.03 g (71%) of a light yellow foam: mp 74°–80° C.; $^1$H NMR (CDCl$_3$) δ 1.39 (s, 9H), 1.44 (d, J=7.2 Hz, 3H), 2.77 (dd, J=4.6, 17.6 Hz, 1H), 3.42 (dd, J=2.5, 17.6 Hz, 1H), 4.1–4.2 (m, 1H), 4.95–5.1 (m, 2H), 7.62 (br d, J=9.2 Hz, 1H), 7.93 (br d, J=9.0 Hz, 2H), 8.18 (d, J=9.0 Hz, 2H), 9.28 (br s, 1H); MS (LSIMS) m/e 425 (46, M$^+$+1), 369 (100); [α]$_D^{20}$ –11.8° (c=1.0, DMF); Analysis calculated for C$_{18}$H$_{24}$N$_4$O$_8$: C, 50.94; H,5.70; N13.20; found: C, 50.86; H, 5.68; N, 12.85.

D. t-BOCValAlaAsp-p-nitroanilide t-BOCAlaAsp-p-nitroanilide (424 mg, 1.00 mmole) was dissolved in neat TFA (10 mL) and stirred at room temperature for 1 hour. The solvent was then evaporated in vacuo and the residue was then dissolved in 10 mL of CH$_2$Cl$_2$ which was then evaporated in vacuo. This dissolution with CH$_2$Cl$_2$ and subsequent evaporation was repeated two more times giving a light yellow foam. This foam was suspended in CH$_2$Cl$_2$ (10 mL) and treated with DIEA (129 mg, 1.00 mmole). To this suspension was added t-BOCVal N-hydroxysuccinimide ester (314 mg, 1.00 mmole), DMF (10 mL) and sufficient additional DIEA to make the mixture neutral. After the mixture was stirred at room temperature for 24 hours, the solvents were removed in vacuo (high vacuum) and the residue triturated with 1N HCl. The resulting light yellow solid was collected, washed with water and dried. Chromatography (5:35:60—acetic acid:ethyl acetate:hexane to 5:55:40—acetic acid:ethyl acetate:hexane) gave 348 mg (66%) of a light yellow glass that was recrystallized from ethyl acetate to give 128 mg of an amorphous solid: mp 200°–202° C.; $^1$H NMR (DMSO-d$_6$) δ 0.78 (d, J=6.7 Hz, 3H), 0.81 (d, J=6.8 Hz, 3H), 1.20 (d, J=8.1 Hz, 3H), 1.37 (s, 9H), 1.85–1.95 (m, 1H), 2.60 (dd, J=7.5, 16.6 Hz, 1H), 2.76 (dd, J=6.3, 16.6 Hz, 1H), 3.75–3.85 (m, 1H), 4.2–4.3 (m, 1H), 4.63 (m, 1H), 6.77 (d, J=8.6 Hz, 1H), 7.88 (d, J=9.2 Hz, 2H), 8.02 (d, J=7.7 Hz, 1H), 8.21 (d, J=9.2 Hz, 2H), 8.41 (d, J=7.0 Hz, 1H), 10.53 (brs 1H); MS (LSIMS) m/e 546 (21, M$^+$+Na), 524 (22, M$^+$+1), 507 (12), 468 (45), 424 (57), 330 (35), 286 (34), 215 (100); [α]$_D^{20}$ –27.7° (c=1.0, DMF); Analysis calculated for C$_{23}$H$_{33}$N$_5$O$_9$: C, 52.76; H, 6.35; N, 13.38; found: C, 52.45; H, 6.57; N, 12.76.

EXAMPLE 5

AcValAlaAsp-p-nitroanilide t-BOCValAlaAsp-p-nitroanilide (174 mg, 0.33 mmole) was dissolved in neat TFA (5 mL) and stirred at room temperature for 1 hour. The TFA was removed in vacuo and the residue was then dissolved in 5 mL of CH$_2$Cl$_2$ which was then evaporated in vacuo. This dissolution with CH$_2$Cl$_2$ and subsequent evaporation repeated two more times. The residue was dissolved in dioxane/water (5 mL, 4:1) and treated with acetic acid N-hydroxysuccinimide ester (63 mg, 0.40 mmole) and NaHCO$_3$ (139 mg, 1.65 mmole). After 18 hours, the mixture was diluted with 1N HCl (25 mL) and extracted three times with ethyl acetate. The combined extracts were dried with MgSO$_4$, filtered and concentrated to a yellow solid which was recrystallized from ethyl acetate/ethanol to give 33 mg (21%) of light yellow powder: mp 196°–200° C. (dec.); $^1$H NMR (DMSO-d$_6$) δ 0.80 (d, J=6.6 Hz, 3H), 0.82 (d, J=5.1 Hz, 3H), 1.20 (d, J=7.2 Hz, 3H), 1.85 (s, 3H), 1.85–2.0 (m, 1H), 2.60 (dd, J=7.5, 16.6 Hz, 1H), 2.75 (dd, J=6.2, 16.6 Hz, 1H), 4.1–4.2 (m, 1H), 4.2–4.3 (m, 1H), 4.6–4.7 (m, 1H), 7.8–7.9 (m, 3H), 8.11 (d, J=6.8 Hz, 1H), 8.21 (d, J=9.3 Hz, 2H), 8.27 (d, J=7.2 Hz, 1H), 10.51 (s, 1H), 12.45 (br s, 1H); MS (LSIMS) m/e 488 (6, M$^+$+Na), 466 (23, M$^+$+1), 449 (7) 328 (15), 213 (44), 142 (100); [α]$_D^{20}$ −24.9° (c=1.0, DMF); Analysis calculated for C$_{20}$H$_{27}$N$_5$O$_8$: C, 51.60; H, 5.85; N, 15.05; found: C, 50.16; H, 5.79; N, 14.06.

EXAMPLE 6

CBZValAlaAsp-p-nitroanilide

A. CBZAsp(β-t-butyl)-p-(t-BOC amino)anilide

CBZAsp(β-t-butyl)OH dicyclohexylamine salt (2.52 g, 5.00 mmole), 4-(t-BOC amino)aniline (1.04 g, 5.00 mmole), DEC.HCl (1.44 g, 7.5 mmole), N-hydroxybenzotriazole hydrate (675 mg, 5.0 mmole) and DIEA (323 mg, 2.5 mmole) were combined in dry DMF (50 mL) and stirred at room temperature for 24 hours. The mixture was diluted with ether (150 mL) and washed twice with 1N HCl, twice with saturated NaHCO$_3$, and once with 1N HCl. After drying over MgSO, filtration and concentration in vacuo, an off-white solid was obtained which was recrystallized from cyclohexane/ethyl acetate to give 2.17 g (84%) of tan solid. An analytical sample was prepared by recrystallization from hexane/ethylacetate: mp 131°–133° C. (softens 120° C.); $^1$H NMR (CDCl$_3$) δ 1.43 (s, 9H), 1.51 (s, 9H), 2.67 (dd, J=7.1, 17.2 Hz, 1H), 2.97 (dd, J=4.1, 17.2 Hz, 1H), 4.6–4.7 (m, 1H), 5.16 (s, 2H), 6.10 (br d, 1H), 6.45 (br s, 1H), 7.30 (d, J=9.1 Hz, 2H), 7.35–7.45 (m, 7H), 8.41 (b s, 1H); MS (LSIMS) m/e 513 (46, M$^+$), 457 (40), 402 (38), 358 (40), 243 (32), 178 (31), 152 (100); [α]$_D^{20}$ −19.2° (c=1.0, methanol); HPLC retention time: 4.32 minutes (30%), 17.17 minutes (40%); Analysis calculated for C$_{27}$H$_{35}$N$_3$O$_7$: C, 63.14; H, 6.87; N, 8.18; found: C, 63.24; H, 6.94; N, 8.05.

B. CBZAlaAsp(β-t-butyl)-p-(t-BOC amino)anilide

CBZAsp(β-t-butyl)-p-(t-BOC amino)anilide (1.17 g, 2.28 mmole) was hydrogenated over 10% Pd-C (120 mg) at 3 atm. in CH$_3$OH (20 mL) at room temperature for 1 hour. The reaction mixture was filtered through a nylon filter and the filtrate concentrated to an oil. This was dissolved in CH$_2$Cl$_2$ (23 mL) and CBZAla N-hydroxysuccinimide ester (803 mg, 2.51 mmole) was added. After being stirred at room temperature for 24 hours, the reaction mixture was washed twice with 1N HCl and twice with saturated NaHCO$_3$ and then dried over MgSO$_4$. Filtration and concentration in vacuo gave a white solid which was recrystallized from cyclohexane/ethyl acetate to give 750 mg (56%) of white powder: mp 183°–185° C. (with gas evolution); $^1$H NMR (DMSO-d$_6$) δ 1.19 (d, J=7.2 Hz, 3H), 1.35 (s, 9H), 1.45 (s, 9H), 2.54 (dd, J=7.7, 15.6 Hz, 1H), 2.72 (dd, J=6.4, 15.6 Hz, 1H), 4.0–4.1 (m, 1H), 4.6–4.7 (m, 1H), 4.99 (d, J=12.5 Hz, 1H), 5.03 (d, J=12.5 Hz, 1H), 7.25–7.4 (m, 7H), 7.48 (d, J=8.9 Hz, 2H), 7.58 (br d, J=6.5 Hz, 1H), 8.23 (d, J=8.1 Hz, 1H), 9.26 (br s, 1H), 9.68 (br s, 1H); MS (LSIMS) m/e 585 (34, M$^+$+1), 584 (44, M$^+$), 529 (41), 528 (29), 473 (50), 321 (94) 243 (100); [α]$_D^{20}$ −28.9° (c=1.0, methanol); Analysis calculated for C$_{30}$H$_{40}$N$_4$O$_8$: C, 61.63; H, 6.90; N, 9.58; found: C, 61.66; H, 7.15; N, 9.52.

C. CBZValAlaAsp(β-t-butyl)-p-(t-BOC amino)anilide

CBZAlaAsp(β-t-butyl)-p-(t-BOC amino)anilide (1.97 g, 3.37 mmole) was hydrogenated over 10% Pd on carbon (200 mg) at 3 atm. in CH$_3$OH (50 mL) at room temperature for 1 hour. The reaction mixture was filtered through a nylon filter and the filtrate concentrated to a white gummy solid. This solid was suspended in DMF (12 mL) and CBZVal N-hydroxysuccinimide ester (1.29 g, 3.71 mmole) was added. After being stirred at room temperature for 24 hours, the reaction mixture was diluted with a saturated solution of NaHCO$_3$ and stirred for 15 minutes. The precipitated product was collected, washed with water and dried under high vacuum to give 2.16 g (94%) of a fine white powder: mp 232°–233° C. (with gas evolution); $^1$NMR (DMSO-d$_6$) δ 0.81 (d, J=8.7 Hz, 3H), 0.84 (d, J=6.9 Hz, 3H), 1.19 (d, J=7.0 Hz, 3H), 1.33 (s, 9H), 1.85–2.0 (m, 1H), 2.52 (dd, J=7.6, 15.8 Hz, 1H), 2.69 (dd, J=6.4, 15.8 Hz, 1H), 3.8–3.9 (m, 1H), 4.2–4.3 (m, 1H), 4.6–4.7 (m, 1H), 5.01 (d, J=12.8 Hz, 1H), 5.03 (d, J=12.8 Hz, 1H), 7.25–7.4 (m, 8H), 7.47 (d, J=9.0 Hz, 2H), 8.08 (br d, J=6.9 Hz, 1H,) 8.21 (br d, J=7.9 Hz, 1H), 9.25 (br s, 1H), 9.79 (br s, 1H); MS (LSIMS) m/e 684 (51, M$^+$), 420 (40), 119 (100); [α]$_D^{20}$ −16.5° (c=1.0, DMF); Analysis calculated for C$_{35}$H$_{49}$N$_5$O$_9$: C, 61.47; H, 7.22; N, 10.24; found: C, 61.29; H, 6.93; N, 10.20.

D. CBZValAlaAsp-p-nitroanilide

CBZValAlaAsp(β-t-butyl)-p-(t-BOC amino)anilide (900 mg, 1.32 mmole) was dissolved in cold TFA (13 mL) and stirred at 0° C. for 4 hours. The TFA was removed in vacuo and acetic acid (26 mL) added to the residue. To the resulting suspension was added NaBO$_3$ (2.03 g, 13.2 mmole) and the mixture stirred for 18 hours at room temperature. The reddish-orange reaction mixture was concentrated. Water and ethyl acetate (200 mL) were added to the residue and a small amount of 1N HCl added to bring the pH to about 1. The separated ethyl acetate layer was twice washed with 1N HCL and was then dried with MgSO$_4$, filtered and concentrated to a light brown solid. This was absorbed onto silica gel and charged onto a column. Elution (2.5:2.5:95—acetic acid:methanol:CH$_2$Cl$_2$) gave 474 mg (64%) of product. Further purification was achieved by preparative thin layer chromatography (5:5:95—acetic acid:methanol:CH$_2$Cl$_2$): mp 204°–206° C. (dec., softens 188° C.); $^1$H NMR (DMSO-d$_6$) δ 0.80 (d, J=8.1 Hz, 3H), 0.83 (d, J=7.0 Hz, 3H), 1.21 (d, J=7.1 Hz, 3H), 1.85–2.0 (m, 1H), 2.61 (dd, J=7.7, 16.6 Hz, 1H), 2.77 (dd, J=6.0, 16.6 Hz, 1H), 3.8–3.9 (m, 1H), 4.2–4.3 (m, 1H), 4.6–4.7 (m, 1H), 5.02 (s, 2H), 7.25–7.4 (m, 6H), 7.88 (d, J=9.3 Hz, 2H), 8.12 (d, J=6.6 Hz, 1H), 8.21 (d, J=9.3 Hz, 2H), 8.38 (d, J=7.3 Hz, 1H), 10.48 (s, 1H), 12.40 (br s, 1H); MS (LSIMS) m/e 580 (M$^+$+Na, 17) 558 (M$^+$+1, 71), 541 (19), 527(32), 420 (51), 305 (100); [α]$_D^{20}$ −23.9° (c=1.0, DMF); Analysis calculated for C$_{26}$H$_{31}$N$_5$O$_9$.0.25H$_2$O:C, 55.56; H, 5.65 N, 12.46; found: C, 55.33; H, 5.56; N, 12.09.

EXAMPLE 7

Assay

The use of the compounds of this invention in identifying inhibitors of interleukin 1β converting enzyme (ICE) and, consequently, demonstrating the latter compounds' effectiveness for treating inflammatory diseases is disclosed by the following in vitro assay. Other procedures for purification and assaying ICE are disclosed in Black et al., *FEBS Letters*, 247, 386–390 (1989), and Thornberry et al., *Nature*, 356, 768–774 (1992).

Cell Culture and Lysates

Human monocyte cell line, THP-1 (ATCC-TIB 202) was grown in RPMI media 1640 (Gibco BRL Gaithersburg, Md. 20877) with 10% fetal bovine serum, harvested by centrifugation, washed twice in Dulbecco's PBS dithiothreitol without $Ca^{++}$, and resuspended in 10 mM Tris-HCl pH 8 buffer containing 5 mM DTT (dithiothreitol), 1 mM EDTA (ethylene diamine tetraacetic acid), 1 mM PMSF (phenylmethyl sulfonylfluoride), 1 µg/ml pepstatin, and 1 µg/ml leupeptin at $1–3\times10^8$ cells per ml. Cells were frozen at –70° C. until use and then lysed by thawing. Lysates were cleared by centrifugation at 20,000×g for 1 hour followed by 120,000×g for 1 hour.

Partial Purification of ICE Activity by Ion-Exchange Chromatography

ICE activity was purified from THP-1 cell lysates by three chromatographic steps: (A) Thp-1 cell lysate (1.5 L) was desalted by G25 column chromatography (Pharmacia LKB Biotechnology) (B) The protein fraction was then subjected to ion-exchange chromatography on Q-Sepharose Fast Flow (Pharmacia LKB Biotechnology) in buffer A (20 mM Tris pH 7.8 containing 5 mM EDTA, 1 mM PMSF, 1 µg/ml pepstatin, and 1 µg/ml leupeptin). ICE activity was eluted with a gradient of NaCl in buffer A. (C) The active fractions from B were desalted, concentrated and subjected to MonoQ (trademark) (Pharmacia LKB Biotechnology) column chromatography. ICE activity was then eluted in a NaCl gradient. Active ICE fractions from C were pooled and used to bind immunoaffinity beads containing covalently linked antibodies raised against the first 11 N-terminal residues of ICE ($NH_2$-Asp-Pro-Ala-Met-Pro-Thr-Ser-Ser-Val-Lys-Leu-Cys-$CONH_2$).

Immobilization of ICE

Immobilization of ICE to immunoaffinity beads was done following standard protocols. Briefly, IgG fractions were covalently linked to protein A beads as described by the manufacturers (Antibody Orientation Kit Protein A Agarose supplied by Affinica (trademark) (Product manufactured by Schleicher and Schuell)). Protein A beads were pelleted by centrifugation and washed with 5 times their volume with Affinica (trademark) supplied "binding buffer". IgG, appropriately diluted in "binding buffer," was then bound to the beads. The beads were then washed and the bound IgG was covalently linked with dimethyl suberimidate. After the reaction was stopped with the "quenching buffer" supplied by Affinica (trademark), the immunoaffinity beads were washed and stored in PBS buffer containing 0.02% $NaN_3$. To bind the immunoaffinity beads with MonoQ purified ICE preparations, the beads were washed in 10 mM Tris HCL buffer pH 7.8 containing 5 mM DDT, 1 mM EDTA-NA, 1 ug/ml peptstatin, 1 ug/ml leupeptin and 10% glycerol ("washing buffer"). After the wash, the beads were mixed with ICE in the presence of 10% DMSO final concentration. The suspension was rotated slowly for 1 hour at room temperature. Subsequently, the beads were thoroughly washed with the "washing buffer" before they were used and resuspended in an equal volume of this buffer in the enzymatic assay.

Assay Procedure

The enzymatic reaction was carded out at 25° C. in 96 microtiter wells (100 µl final volume) with active enzyme immobilized to anti-ICE antibodies covalently linked to protein A beads as described above. The incubation mixtures for the enzymatic assays contained 0.01 to 1.5 mM of the pNA substrates and was made up in 8.35 mM MES, 4.17 mM Tris, 4.17 mM acetic acid, 4.6M DMSO, 0.8 mM EDTA and 4.17 mM DTT (final concentrations) adjusted to a final pH of 7.

The enzymatic reaction was monitored spectrophotometrically at 405 nM. The increase in absorbance at this wave length resulted from the release of pNA chromophore after hydrolysis by ICE of the peptidic-pNA substrate. The release of the chormophore was linear with reaction time and the rates observed were proportional to ICE and substrate concentration. The spectrophotometric assay greatly facilitated the quantitative determination of kinetic constants and assessment of the enzyme specificity (Vmax/Km). In addition, comparison of inhibitory compounds was possible. These compounds could easily be introduced in the assay and compared as to the type (competitive, uncompetitive, mixed) and degree (Ki) of inhibition they can effect on catalysis (See A. Cornish-Bowden, *Fundamentals of Enzyme Kinetics*, Butterworth and Co., Ltd., London (1979).

The rates, kinetic constants and relative specificity for the pNA substrates for ICE are presented in Table 1. The data are consistent with the interpretation that tripeptides and tetrapeptides are substrates for this enzyme, compounds smaller than tripeptides are not. In addition two known peptidic compounds (prepared by a solid phase peptide synthesizer) known to be hydrolyzed by ICE, p70 (H-Asn-Glu-Ala-Tyr-Val-His-Asp-Ala-Pro-Val-Arg-Ser-Leu-Asn and p48 (Ac-Tyr-Val-His-Asp-Ala-$NH_2$), were also found to behave as competitive inhibitors of the hydrolysis of CBZ-Val-Ala-Asp-pNA by affecting Km but not Vmax (Ki(mM) was found to be 0.46 mM and 1.6 mM respectively). This demonstrated the ability of the assay to quantitatively evaluate potential inhibitors of ICE.

TABLE 1

Evaluation of pNA Substrates

| Compound of Example | Increase In Absorbance Rates (mOD/min) | Km (mM) | mOD/min Vmax (Rates) | Vmax/Km | Relative Vmax/Km |
| --- | --- | --- | --- | --- | --- |
| 4 | 0.17 | 0.10 | 0.443 | 0.24 | 0.54 | 1.00 |
| 5 | 0.15 | 0.08 | 0.447 | 0.25 | 0.56 | 1.04 |
| 6 | 0.18 | 0.15 | 0.0979 | 0.21 | 2.15 | 3.98 |
| 1 | 0.21 | 0.17 | 0.0438 | 0.27 | 6.16 | 11.41 |

We claim:

1. A method of detecting inhibitors of interleukin 1β converting enzyme (ICE) comprising evaluating a compound's capacity to inhibit the ICE-induced hydrolysis of a para-nitroanilide peptide selected from the group consisting of PhCH₂CH₂COValAlaAsp-p-nitroanilide, PhCH₂NHCoValAlaAsp-p-nitroanilide, t-BOCValAlaAsp-p-nitroanilide, AcValAlaAsp-p-nitroanilide and CBZValAlaAsp-p-nitroanilide by:

a) mixing active ICE immobilized to anti-ICE antibodies covalently linked to protein A beads with said para-nitroanilide peptide in the presence or absence of said compound in a reaction vessel, and b) monitoring enzymatic activity spectrophotometrically at 405 nm.

\* \* \* \* \*